United States Patent [19]

Pitt

[11] 4,035,490
[45] July 12, 1977

[54] INSECTICIDE COMPOSITIONS

[75] Inventor: Leland S. Pitt, San Jose, Calif.

[73] Assignee: Stauffer Chemical Company, Westport, Conn.

[21] Appl. No.: 605,692

[22] Filed: Aug. 18, 1975

[51] Int. Cl.² ............................ A01N 9/02; A01N 9/22; A01N 9/36
[52] U.S. Cl. ............................... 424/225; 424/274
[58] Field of Search ............ 424/225, 274; 260/964

[56] References Cited

PUBLICATIONS

Chemical Week, Apr. 26, 1969 p. 51.
Flynn et al., Chem. Abst. vol. 55 (1961) pp. 4864–4865.
Metcalf et al., Chem. Abst. vol. 44 (1950) and subject p. 9606s.

*Primary Examiner*—Allen J. Robinson
*Attorney, Agent, or Firm*—Joel G. Ackerman

[57] ABSTRACT

The effect of the compound

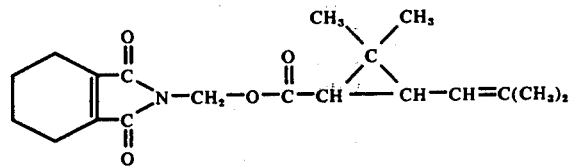

as an insecticide is enchanced by the addition of a compound of the formula

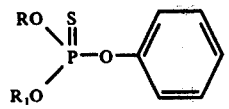

wherein R and $R_1$ are methyl or ethyl.

8 Claims, No Drawings

INSECTICIDE COMPOSITIONS

It has been found in the past that the activity of a known insecticide can be enhanced by the addition of, or mixing with, one or more other substances which, are not themselves active as insecticides. For instance, U.S. Pat. No. 3,830,887 discloses such compounds which serve to enhance the activity of N-(mercaptomethyl) phthalimide-S-(O,O-dimethylphosphorodithioate).

This invention relates to improved insecticidal compositions. More particularly, this invention relates to improved insecticidal compositions in which the insecticidal activity of the compound 2,3,4,5-tetrahydrophthalimidomethyl chrysanthemate, i.e.

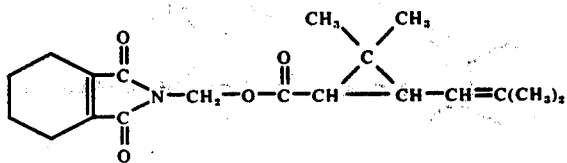

(hereinafter referred to as 2,3,4,5-TPMC), a commercially available insecticide also known as phthalthrin, is enhanced by adding or mixing thereto an activating amount of a substance having the formula

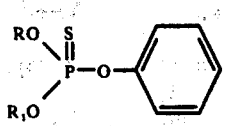

in which R and $R_1$ are methyl or ethyl.

By the term "activating amount" is meant an amount of the activating substance which increases the insecticidal activity of the known insecticide against the particular insect in question.

The activators herein are prepared by reacting an appropriate phenol with a dialkoxyhalo phosphono derivative. After the reaction has been completed, the products are isolated, purified and admixed with the 2,3,4,5-TPMC. The amount of activator admixed therewith can range between about 1:0.1 up to about 1:10 parts by weight of insecticide to activator. After the insecticide and activator are mixed together, they are applied to the habitat of the insect in a conventional manner.

Preparation of compounds which serve as activators for 2,3,4,5-TPMC is illustrated as follows.

EXAMPLE 1

O,O-Dimethyl-O-phenyl phosphorothioate

To a solution of 9.4 grams (0.1 mole) phenol in 100 ml tetrahydrofuran was added 4.4 grams (0.11 mole) powdered NaOH and stirred until clear. A solution of 16.0 grams (0.1 mole) O,O-dimethyl phosphorochloridothionate in 25 ml tetrahydrofuran was added slowly to the sodium phenylate solution and refluxed for 30 minutes. Benzene (100 ml) was added to the mixture. The resulting mixture was washed with 10% NaOH and twice with $H_2O$, dried over anhydrous $MgSO_4$ and the volatiles removed under reduced pressure to yield 20.2 grams, $N_D^{30}$ 1.5327.

EXAMPLE 2

O-O-Diethyl-O-phenyl O,O-Diethyl-O-phenyl phosphorothioate

The procedure of Example 1 was repeated, except that (18.9 grams, 0.1 mole) O,O-diethyl phosphorochloridothioate was used. The yield was 24.6 grams, $N_D^{30} = 1.5077$.

Insecticide Evaluation

A. Housefly (*Musca domestica*, Linné) (HF in Table below)

The following procedure was used to test susceptible houseflies. Stock solutions containing both 2,3,4,5-TPMC and activator were prepared using acetone as a solvent. Ratios of insecticide:activator ranged from 1:0 to 1:0.1. The stock solutions were then diluted to appropriate concentrations and aliquots pipetted into 55mm-diameter aluminum dishes. One ml of 0.2% peanut oil in acetone was also dispensed into each aluminum dish to ensure an even distribution of the test compounds. A toxicant/activator film residue formed in the dish as the solvents evaporated. The dishes were then placed in a circular cardboard cage, closed on the bottom with cellophane and covered on top with cloth netting. Twenty-five female houseflies were introduced into the cage and the percent mortality recorded after 48 hours. $LD_{50}$ values are expressed in terms of μg of insecticide per 25 (female) flies. Controls were also run identically to the above with the exception that in one set of controls only 2,3,4,5-TMPC was used, and in another set only the activator was used.

B. German cockroach (*Blatella germanica*, Linné) (GC in Table below)

Stock solutions containing both 2,3,4,5-TPMC and activator were prepared using a 50:50 acetone:water solution as a solvent. Ratios of insecticide:activator ranged from 1:10 to 1:0.1. The stock solutions were then diluted to appropriate concentrations, and 2 cc aliquots sprayed through a DeVilbiss-type EGA hand spray gun into circular cardboard cages containing ten one-month old German cockroach nymphs. The test cages were covered on the bottom with cellophane and on the top with tulle netting. Concentrations tested ranged from 0.1% insecticide down to that at which 50% mortality is obtained. The percent mortality was recorded two days later. Controls were run identically to the above, with the exception that in one control only 2,3,4,5-TPMC was used, and in another control only the activator.

The results of these tests are shown in the following table.

| O,O-Dimethyl-O-phenyl phosphorothioate (Compound 1) | | |
|---|---|---|
| | HF | GR |
| 2,3,4,5-TPMC $LD_{50}$ | 4.2 | 0.3 |
| Compound 1 $LD_{50}$ | >200.0 | >1.0 |
| 2,3,4,5-TPMC + Compound 1 (1:0.1) $LD_{50}$ | 3.8 | .08 |
| Activating Factor | >1.1 | >3.64 |
| 2,3,4,5-TPMC + Compound 1 (1:0.5) $LD_{50}$ | 3.8 | .08 |
| Activating Factor | >1.1 | >3.26 |
| 2,3,4,5-TPMC + Compound 1 (1:1) $LD_{50}$ | 3.5 | .08 |
| Activating Factor | >1.2 | >2.88 |
| 2,3,4,5-TPMC + Compound 1 (1:5) $LD_{50}$ | 3.5 | .02 |
| Activating Factor | >1.1 | >6.00 |
| 2,3,4,5-TPMC + Compound 1 (1:10) $LD_{50}$ | 2.80 | .008 |
| Activating Factor | >1.2 | >9.38 |
| O,O-Diethyl-O-phenyl-phosphorothioate (Compound 2) | | |

-continued

|  | HF | GR |
|---|---|---|
| 2,3,4,5-TPMC LD$_{50}$ | 4.2 | .3 |
| Compound 2 LD$_{50}$ | >200.0 | >1.0 |
| 2,3,4,5-TPMC + Compound 2 (1:.1) LD$_{50}$ | 2.8 | .08 |
| Activating Factor | >1.5 | >3.64 |
| 2,3,4,5-TPMC + Compound 2 (1:.5) | 2.5 | .02 |
| Activating Factor | >1.66 | >13.04 |
| 2,3,4,5-TPMC + Compound 2 (1:1) | 2.2 | .01 |
| Activating Factor | >1.8 | >23.07 |
| 2,3,4,5-TPMC + Compound 2 (1:5) | 2.5 | .008 |
| Activating Factor | >1.5 | >15.0 |
| 2,3,4,5-TPMC + Compound 2 (1:10) | 2.0 | .008 |
| Activating Factor | >1.7 | >9.38 |

The Activating Factor (A.F.) is arrived at by using the following formula from the expected response for a given combination of two insecticides:

$$\text{A.F.} = \frac{\text{LD}_{50} \text{ of Insecticide} \frac{1}{(xy+1)}}{\text{Experimental LD}_{50} \text{ of Combination}}$$

in which X = the ratio of the percent or weight of the activator to the percent or weight of the insecticide. Y = the ratio of the LD$_{50}$ of the insecticide to the LD$_{50}$ (highest value tested) of the activator. The experimental LD$_{50}$ of the combination is in terms of the insecticide only.

The A.F. is therefore the ratio of the expected LD$_{50}$ of the combination divided by the experimental LD$_{50}$. It is noted that when the observed response is greater than the expected response, the A.F. is greater than 1.

What is claimed is:

1. An insecticidal composition comprising: (a)

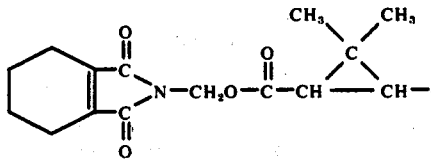

and (b) a compound having the formula

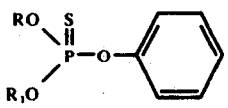

wherein R and R$_1$ are methyl or ethyl in a weight ratio of (a):(b) of 1:0.1 – 1:10.

2. The composition of claim 1 wherein R and R$_1$ are methyl.

3. The composition of claim 1 wherein R and R$_1$ are ethyl.

4. A process of controlling insects comprising applying to the insects or habitat thereof an insecticidally effective amount of a composition comprising: (a)

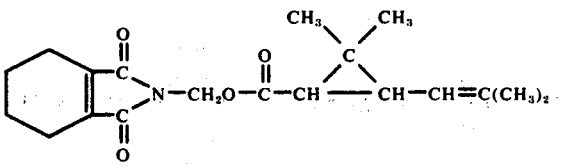

and (b) a compound having the formula

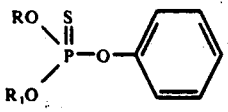

wherein R and R$_1$ are methyl or ethyl in a weight ratio of (a):(b) of 1:0.1 – 1:10.

5. The process according to claim 4 wherein R and R$_1$ are methyl.

6. The process according to claim 4 wherein R and R$_1$ are ethyl.

7. The process according to claim 4 in which the insects are Musca domestica.

8. The process according to claim 4 in which the insects are Blatella germanica.

* * * * *